US007546918B2

(12) United States Patent
Gollier et al.

(10) Patent No.: US 7,546,918 B2
(45) Date of Patent: Jun. 16, 2009

(54) PEELABLE SEAL

(75) Inventors: Paul Andre Gollier, Brussels (BE); Patrick Balteau, Evelette (BE); Vincent Houwaert, Mont-St-Aubert (BE); Francesco Peluso, Heverlee (BE)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 163 days.

(21) Appl. No.: 11/613,011

(22) Filed: Dec. 19, 2006

(65) Prior Publication Data

US 2007/0088314 A1 Apr. 19, 2007

Related U.S. Application Data

(63) Continuation of application No. 10/273,825, filed on Oct. 17, 2002, now Pat. No. 7,175,614.

(51) Int. Cl.
*B65D 30/02* (2006.01)
*A61B 19/00* (2006.01)

(52) U.S. Cl. ........................ 206/219; 604/410; 383/210

(58) Field of Classification Search ................. 206/219, 206/221, 222, 469; 383/210, 211; 604/87, 604/89, 408, 410, 416
See application file for complete search history.

(56) References Cited

U.S. PATENT DOCUMENTS

| | | | |
|---|---|---|---|
| 2,714,974 | A | 8/1955 | Sawyer |
| 2,907,173 | A | 10/1959 | Robbins |
| 3,023,857 | A | 3/1962 | Robbins |
| 3,028,000 | A | 4/1962 | Clements et al. |
| 3,036,894 | A | 5/1962 | Forestiere |
| 3,074,544 | A | 1/1963 | Bollmeier et al. |
| 3,113,986 | A | 12/1963 | Breslow et al. |
| 3,120,336 | A | 2/1964 | Whatley, Jr. |
| 3,149,943 | A | 9/1964 | Amador |
| 3,190,499 | A | 6/1965 | Dow |
| 3,257,072 | A | 6/1966 | Reynolds |
| 3,294,227 | A | 12/1966 | Schneider et al. |
| 3,324,663 | A | 6/1967 | McLean |
| 3,474,898 | A | 10/1969 | Montgomery |
| 3,608,709 | A | 9/1971 | Pike |
| 3,692,493 | A | 9/1972 | Terasaki |
| 3,708,106 | A | 1/1973 | Sargent |
| 3,749,620 | A | 7/1973 | Montgomery |

(Continued)

FOREIGN PATENT DOCUMENTS

| | | |
|---|---|---|
| BE | 894 377 | 1/1983 |

(Continued)

OTHER PUBLICATIONS

English Translation of JP 2001-097394.

(Continued)

*Primary Examiner*—David T Fidei
(74) *Attorney, Agent, or Firm*—Ira D. Finkelstein; K & L Gates LLP

(57) ABSTRACT

The present invention provides a peelable seal for a multi-chambered container including a first edge and a second edge. At least one of the first edge or second edge includes a stress bearing portion and a non-stress bearing portion.

14 Claims, 6 Drawing Sheets

U.S. PATENT DOCUMENTS

| | | | |
|---|---|---|---|
| 3,879,492 | A | 4/1975 | Bontinick |
| 3,950,158 | A | 4/1976 | Gossett |
| 3,983,994 | A | 10/1976 | Wyslotsky |
| 4,000,996 | A | 1/1977 | Jordan |
| 4,226,330 | A | 10/1980 | Butler |
| 4,226,952 | A | 10/1980 | Halasa et al. |
| 4,458,811 | A | 7/1984 | Wilkinson |
| 4,496,046 | A | 1/1985 | Stone et al. |
| 4,519,499 | A | 5/1985 | Stone et al. |
| 4,548,606 | A | 10/1985 | Larkin |
| 4,602,910 | A | 7/1986 | Larkin |
| 4,608,043 | A | 8/1986 | Larkin |
| 4,629,080 | A | 12/1986 | Carveth |
| 4,731,053 | A | 3/1988 | Hoffman |
| 4,770,295 | A | 9/1988 | Carveth et al. |
| 4,795,265 | A | 1/1989 | Dahlberg et al. |
| 4,798,605 | A | 1/1989 | Steiner et al. |
| 4,929,449 | A | 5/1990 | Veech |
| 4,961,495 | A | 10/1990 | Yoshida et al. |
| 4,997,083 | A | 3/1991 | Loretti et al. |
| 5,114,004 | A | 5/1992 | Isono et al. |
| 5,128,414 | A | 7/1992 | Hwo |
| 5,176,634 | A | 1/1993 | Smith et al. |
| 5,186,998 | A | 2/1993 | Eugster |
| 5,195,658 | A | 3/1993 | Hoshino |
| 5,207,320 | A | 5/1993 | Allen |
| 5,207,509 | A | 5/1993 | Herbert |
| 5,209,347 | A | 5/1993 | Fabisiewicz et al. |
| 5,215,214 | A | 6/1993 | Lev et al. |
| 5,257,985 | A | 11/1993 | Puhl |
| 5,263,609 | A | 11/1993 | Hoshino |
| 5,267,646 | A | 12/1993 | Inoue et al. |
| 5,287,961 | A | 2/1994 | Herran |
| 5,334,180 | A | 8/1994 | Adolf et al. |
| 5,353,927 | A | 10/1994 | Stupar et al. |
| 5,391,163 | A | 2/1995 | Christine et al. |
| 5,423,421 | A | 6/1995 | Inoue et al. |
| 5,462,526 | A | 10/1995 | Barney et al. |
| 5,474,818 | A | 12/1995 | Ulrich et al. |
| 5,478,617 | A | 12/1995 | Watanabe et al. |
| 5,482,771 | A | 1/1996 | Shah |
| 5,492,219 | A | 2/1996 | Stupar |
| 5,494,190 | A | 2/1996 | Boettcher |
| 5,501,887 | A | 3/1996 | Tanaka et al. |
| 5,509,898 | A | 4/1996 | Isono et al. |
| 5,514,123 | A | 5/1996 | Adolf et al. |
| 5,520,975 | A | 5/1996 | Inoue et al. |
| 5,577,369 | A | 11/1996 | Becker et al. |
| 5,610,170 | A | 3/1997 | Inoue et al. |
| 5,706,937 | A | 1/1998 | Futagawa et al. |
| 5,728,681 | A | 3/1998 | Kido et al. |
| 5,792,213 | A | 8/1998 | Bowen |
| 5,837,336 | A | 11/1998 | Ichimura et al. |
| 5,843,049 | A | 12/1998 | Heilmann et al. |
| 5,853,388 | A | 12/1998 | Semel |
| 5,865,309 | A | 2/1999 | Futagawa et al. |
| 5,910,138 | A | 6/1999 | Sperko et al. |
| 5,928,213 | A | 7/1999 | Barney et al. |
| 5,944,709 | A | 8/1999 | Barney et al. |
| 5,967,308 | A | 10/1999 | Bowen |
| 6,004,636 | A | 12/1999 | Nicola et al. |
| 6,007,529 | A | 12/1999 | Gustafsson et al. |
| 6,017,598 | A | 1/2000 | Kreischer et al. |
| 6,039,719 | A | 3/2000 | Wieslander et al. |
| 6,039,720 | A | 3/2000 | Wieslander |
| 6,117,123 | A | 9/2000 | Barney et al. |
| 6,129,925 | A | 10/2000 | Kido et al. |
| 6,149,655 | A | 11/2000 | Constantz et al. |
| 6,162,205 | A | 12/2000 | Shichi et al. |
| 6,165,161 | A | 12/2000 | York et al. |
| 6,186,998 | B1 | 2/2001 | Inuzuka et al. |
| 6,203,535 | B1 | 3/2001 | Barney et al. |
| 6,231,559 | B1 | 5/2001 | Loretti |
| 6,245,176 | B1 | 6/2001 | Greenland |
| 6,269,979 | B1 | 8/2001 | Dumont |
| 6,280,431 | B1 | 8/2001 | Domkowski et al. |
| 6,297,046 | B1 | 10/2001 | Smith et al. |
| 6,309,673 | B1 | 10/2001 | Duponchelle et al. |
| 6,341,802 | B1 | 1/2002 | Matkovich |
| 6,398,771 | B1 | 6/2002 | Gustafsson et al. |
| 6,399,704 | B1 | 6/2002 | Laurin et al. |
| 6,468,259 | B1 | 10/2002 | Loretti et al. |
| 6,484,874 | B1 | 11/2002 | Kageyama et al. |
| 6,491,159 | B2 | 12/2002 | Shibata |
| 6,645,191 | B1 | 11/2003 | Knerr et al. |
| 6,743,451 | B2 | 6/2004 | Rasile et al. |
| 6,846,305 | B2 | 1/2005 | Smith et al. |
| 7,175,614 | B2 * | 2/2007 | Gollier et al. ............... 604/410 |
| 2001/0000042 | A1 | 3/2001 | Inuzuka et al. |
| 2002/0052280 | A1 | 5/2002 | Komatsu |
| 2002/0094141 | A1 | 7/2002 | Hoshino |
| 2002/0115795 | A1 | 8/2002 | Shang et al. |
| 2002/0122933 | A1 | 9/2002 | Takahata et al. |
| 2002/0138066 | A1 | 9/2002 | Manica et al. |
| 2003/0047467 | A1 | 3/2003 | Smith et al. |
| 2003/0146115 | A1 | 8/2003 | Sharp |
| 2004/0078023 | A1 | 4/2004 | Gollier et al. |

FOREIGN PATENT DOCUMENTS

| | | |
|---|---|---|
| BR | 9 905 055 | 6/2001 |
| DK | DE 44 10 876 | 10/1995 |
| DK | DE 691 11 430 | 1/1996 |
| DK | DE 298 14 215 | 10/1998 |
| DK | DE 694 10 351 | 10/1998 |
| DK | DE 198 11 276 | 1/2000 |
| DK | DE 199 03 705 | 7/2000 |
| DK | DE 201 11 308 | 12/2001 |
| EP | 0 345 774 | 12/1989 |
| EP | 0 444 900 | 9/1991 |
| EP | 0 513 364 | 11/1992 |
| EP | 0 605 220 A2 | 7/1994 |
| EP | 0 619 998 | 10/1994 |
| EP | 0 634 270 | 1/1995 |
| EP | 0 639 364 | 2/1995 |
| EP | 0 605 220 B1 | 9/1997 |
| EP | 0 875 231 | 4/1998 |
| EP | 0 541 715 | 5/1999 |
| EP | 0 920 849 | 6/1999 |
| EP | 0 972 506 | 1/2000 |
| EP | 0 845 969 | 11/2000 |
| EP | 1 103 487 | 11/2000 |
| EP | 1 070 495 | 1/2001 |
| EP | 1 101 483 | 5/2001 |
| EP | 1 106 644 | 6/2001 |
| EP | 0 898 466 | 12/2001 |
| EP | 1 161 932 | 12/2001 |
| EP | 1 101 483 | 3/2002 |
| EP | 1 0111 605 | 7/2002 |
| GB | 2 134 067 | 8/1984 |
| JP | 01-240469 | 9/1989 |
| JP | 0 2004671 | 1/1990 |
| JP | 0 3000667 | 1/1991 |
| JP | 0 3289478 | 12/1991 |
| JP | 04-097751 | 3/1992 |
| JP | 0 5068702 | 3/1993 |
| JP | 05-068702 | 3/1993 |
| JP | 0 5294350 | 11/1993 |
| JP | 0 6039018 | 2/1994 |
| JP | 06-039018 | 2/1994 |
| JP | 0 7132946 | 5/1995 |
| JP | 0 7155363 | 6/1995 |
| JP | WO 95/26117 | 9/1995 |
| JP | 07-303694 | 11/1995 |

| | | |
|---|---|---|
| JP | 08-100089 | 4/1996 |
| JP | 08-215285 | 8/1996 |
| JP | 08-229101 | 9/1996 |
| JP | 0 8257102 | 10/1996 |
| JP | 0 8280774 | 10/1996 |
| JP | 0 8280775 | 10/1996 |
| JP | 08-280774 | 10/1996 |
| JP | 09-010282 | 1/1997 |
| JP | 0 9084853 | 3/1997 |
| JP | 0 9108304 | 4/1997 |
| JP | 0 9108309 | 4/1997 |
| JP | 09-122205 | 5/1997 |
| JP | 09-176336 | 7/1997 |
| JP | 09-327498 | 12/1997 |
| JP | 10-015033 | 1/1998 |
| JP | 10-024087 | 1/1998 |
| JP | 10-024088 | 1/1998 |
| JP | 10005313 | 1/1998 |
| JP | 10024088 | 1/1998 |
| JP | 10-043272 | 2/1998 |
| JP | 10-071185 | 3/1998 |
| JP | 10071185 | 3/1998 |
| JP | 10-085305 | 4/1998 |
| JP | 10-085306 | 4/1998 |
| JP | 10-108893 | 4/1998 |
| JP | 10085305 | 4/1998 |
| JP | 10129682 | 5/1998 |
| JP | 10-179689 | 7/1998 |
| JP | 10192365 | 7/1998 |
| JP | 10-201819 | 8/1998 |
| JP | 10-201820 | 8/1998 |
| JP | 10-201821 | 8/1998 |
| JP | 10-216200 | 8/1998 |
| JP | 10-218252 | 8/1998 |
| JP | 10201820 | 8/1998 |
| JP | 10201821 | 8/1998 |
| JP | 10216200 | 8/1998 |
| JP | 10-236541 | 9/1998 |
| JP | 10-243990 | 9/1998 |
| JP | 10-277132 | 10/1998 |
| JP | 11-009659 | 1/1999 |
| JP | 11-076367 | 3/1999 |
| JP | 11-079258 | 3/1999 |
| JP | 11-114016 | 4/1999 |
| JP | 11-155930 | 6/1999 |
| JP | 11155930 | 6/1999 |
| JP | 11227842 | 8/1999 |
| JP | 11-285518 | 10/1999 |
| JP | 2000-005276 | 1/2000 |
| JP | 2000-007050 | 1/2000 |
| JP | 2000-014746 | 1/2000 |
| JP | 2000007050 | 1/2000 |
| JP | 2000167022 | 6/2000 |
| JP | 2000-187111 | 7/2000 |
| JP | 2000-262589 | 9/2000 |
| JP | 2000-262591 | 9/2000 |
| JP | 2000-316951 | 11/2000 |
| JP | 2000-390350 | 11/2000 |
| JP | 2003-009350 | 11/2000 |
| JP | 2000316951 | 11/2000 |
| JP | 2001-046470 | 2/2001 |
| JP | 2001054553 | 2/2001 |
| JP | 2001-097394 | 4/2001 |
| JP | 2002-052065 | 2/2002 |
| JP | 2002-136570 | 5/2002 |
| JP | 2002-160771 | 6/2002 |
| JP | 2002-165862 | 6/2002 |
| JP | 2002165862 | 6/2002 |
| JP | 2002165864 | 6/2002 |
| JP | 2002179008 | 6/2002 |
| JP | 2002-200140 | 7/2002 |
| WO | WO 83/01569 | 5/1983 |
| WO | WO 90/14293 | 11/1990 |
| WO | WO 92/02271 | 2/1992 |
| WO | WO 94/16664 | 8/1994 |
| WO | WO 95/07665 | 3/1995 |
| WO | WO 97/05851 | 2/1997 |
| WO | WO 97/05852 | 2/1997 |
| WO | WO 97/37628 | 10/1997 |
| WO | WO 97/42897 | 11/1997 |
| WO | WO 98/10733 | 3/1998 |
| WO | WO 98/16183 | 4/1998 |
| WO | WO 98/34842 | 8/1998 |
| WO | WO 99/23966 | 5/1999 |
| WO | WO 99/24086 | 5/1999 |
| WO | WO 99/27885 | 6/1999 |
| WO | WO 00/30850 | 6/2000 |
| WO | WO 00/57935 | 10/2000 |
| WO | WO 01/08732 | 2/2001 |
| WO | WO 01/35898 | 5/2001 |
| WO | WO 01/89478 | 11/2001 |
| WO | WO 02/01129 | 1/2002 |
| WO | WO 02/051718 | 7/2002 |

OTHER PUBLICATIONS

English Translation of JP 2000-390350.
Partial English Translation of EP 1 103 487.

* cited by examiner

PEELABLE SEAL

The present application is a continuation of U.S. patent application Ser. No. 10/273.825 filed on Oct. 17. 2002 now U.S. Pat. No. 7,175,614, the content of which is expressly incorporated by reference.

BACKGROUND OF THE INVENTION

The present invention relates to a container for delivering fluids. In particular, it relates to a peelable seal between chambers of a multiple chambered container to separately store two or more components for administering to a patient. The components can be in a powder or liquid form and are typically mixed together to form a therapeutic solution. Such solutions can include intravenous solutions, nutritional solutions, drug solutions, enteral solutions, parenteral solutions, dialysis solutions, pharmacological agents including gene therapy and chemotherapy agents, and many other fluids that may be administered to a patient.

Due to stability, compatibility, or other concerns, some medical solutions have to be stored separately prior to administration to a patient. These solutions may be stored in separate containers, but are often stored in separate chambers of a single container. The chambers and solutions are often separated by a frangible heat seal. Examples of such containers are disclosed in U.S. Pat. Nos. 5,209,347; 5,176,634; and 4,608,043. These prior art containers have frangible seals to permit the seal to be broken by hand pressure against the sides of the bag to force the contents to break the seal and permit mixing between the components. Peelable seals are among the frangible seals used that permit the seal to be separated by pulling on opposite sides of the container, or by squeezing the container sidewalls.

The chambered container is typically made of flexible polymeric materials. Numerous polymeric films have been developed for use in such containers, and can be a monolayer structure or a multiple layer structure. The monolayer structure can be made from a single polymer, or from a polymer blend. Multiple layer structures can be formed by co-extrusion, extrusion lamination, lamination, or any suitable means. The multiple layer structures can include layers such as a solution contact layer, a scratch resistant layer, a barrier layer for preventing permeation of oxygen or water vapor, tie layers, or other layers. Selection of the appropriate film depends on the solution to be contained within the container.

The container is typically formed by placing one or more polymeric film sheets in registration by their peripheral portions and sealing the outer periphery to form a fluid tight pouch. The peripheral seals are permanent, and therefore, do not peel. The sheets are sealed by heat sealing, radio frequency sealing, thermal transfer welding, adhesive sealing, solvent bonding, and ultrasonic or laser welding.

Blown extrusion is another method used to make the pouch. Blown extrusion is a process that provides a moving tube of extrudate exiting an extrusion die. Air under pressure inflates the tube. Longitudinal ends of the tube are sealed to form the pouch. A blown extrusion process only requires forming seals along two peripheral surfaces, where the single or multiple sheet registration method requires seals along one, three, or four peripheral surfaces to form the pouch.

A peelable seal having a peel strength lower than the peripheral seal can be formed in the container by various methods such as using a lower heat sealing temperature than used to form the peripheral seal. A peelable seal typically has an initial or peak peel force required to initiate separation of the peelable seal, and a plateau force to propagate the separation. Before steam sterilization, these forces are essentially equal. After the chambered container is filled with solution, it is typically steam sterilized at a temperature of 121° C. During steam sterilization, stress is applied to the edges of the peelable seal. When stress is applied to the peelable seal at a temperature above the softening point of the container material during sterilization, deformation occurs at the seal edge. The deformation reduces stress concentrations at the edge of the seal, increasing the peak peel force necessary to initiate peeling of the peelable seal. After steam sterilization, the peak peel force can be significantly greater than the plateau force. This increased peak peel force is detrimental to use of the multichambered container by making it more difficult to initiate peeling to open the container. This is especially true for patients using the medical solutions who may be infirmed or elderly and unable to provide the force necessary to initiate peeling. Moreover, the peak peel force is difficult to control, some containers remaining easy to initiate peeling in the peelable seal, while others becoming almost impossible to initiate by hand.

SUMMARY OF THE INVENTION

The present invention provides a multichambered container including a first sidewall and a second sidewall. The first sidewall and second sidewall are sealed along a common periphery. It also includes a peelable seal connecting the first sidewall and second sidewall to form chambers in the container. The peelable seal has a length, and a serrated portion along at least a portion of its length.

In another embodiment, the present invention provides a multichambered container including a first sidewall and a second sidewall. The first sidewall and second sidewall are sealed along a common periphery. It also includes a pair of seals connecting the first sidewall and second sidewall to form chambers in the container. The pair of seals includes a first seal and a second seal. The first seal has a first peel force, and the second seal has a second peel force. The first peel force is less than the second peel force.

In a further embodiment, the present invention provides a multichambered container including a first sidewall and a second sidewall. The first sidewall and second sidewall are sealed along a common periphery. A peelable seal connects the first sidewall and second sidewall to form chambers in the container. The peelable seal has outer edges and a central portion. The peelable seal also has a peel force gradient such that the peel force is less at the outer edges than in the central portion.

In another embodiment, the present invention provides a method of peeling a container having a peelable seal. The method includes the steps of providing a container having a first sidewall and a second sidewall and a peelable seal connecting the first sidewall and second sidewall. The peelable seal has a serrated portion along at least a portion of its length. The serrated portion has outer points, inner points, and angular legs connecting the inner points and outer points. The method also includes the step of separating the first sidewall and second sidewall such that the first sidewall and second sidewall separate first along the inner points.

In an additional aspect, the present invention includes a peelable seal for a multi-chambered container comprising a first edge and a second edge. At least one of the first edge or second edge includes a stress-bearing portion and a non-stress bearing portion.

The present invention provides a peelable seal having an initial peak peel force less than or equal to a plateau force needed to propagate peeling. It also provides a controllable, reproducible peak peel force. Additional features and advantages of the present invention are described in, and will be apparent from, the following Detailed Description of the Invention and the figures.

DETAILED DESCRIPTION OF THE INVENTION

Figure 1:
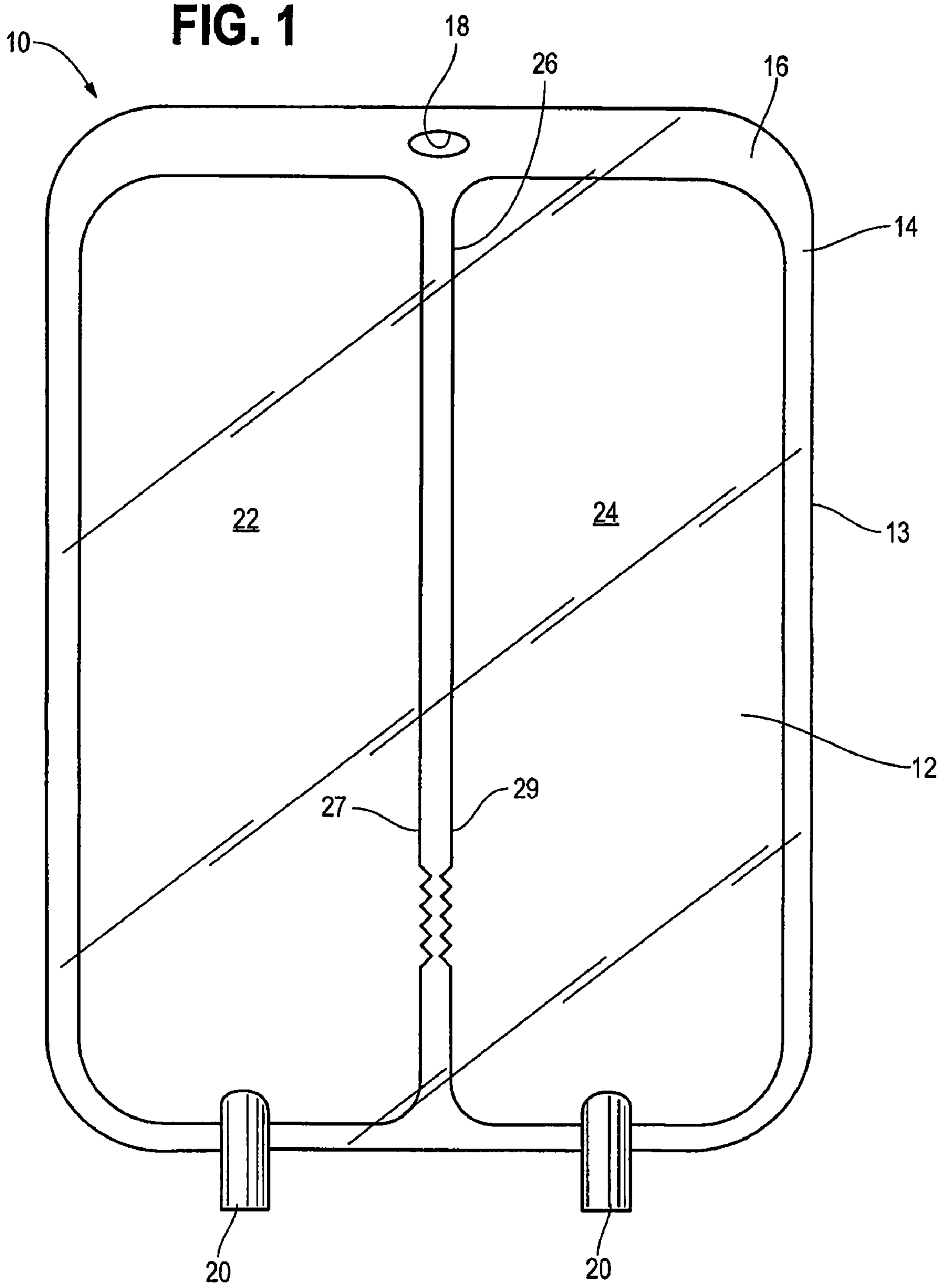
FIG. 1 is a plan view of a multichambered container including a peelable seal in accord with an embodiment of the present invention.

FIG. 1 shows an example of a chambered container 10 of the type used in connection with the present invention. The container 10 stores components that must be kept separate until mixed before administering them to a patient. The container 10 has a first sidewall 12 and a second sidewall 13 sealed along a common periphery 14. The peripheral seal 14 is preferably created by conductive heat sealing, but may be created by adhesive bonding, radio frequency sealing, thermal transfer welding, solvent bonding, ultrasonic or laser welding, or other suitable means.

The peripheral seal 14 may have an expanded portion 16 that includes a cutout 18 for hanging the container 10 from a hook or other means (not shown). The container 10 also includes one or more ports 20 from which the solution contained in the container 10 may be administered to a patient. The container 10 has two or more chambers 22 and 24 separated by a peelable seal 26. The container 10 of FIG. 1 has two chambers 22 and 24, but any suitable number of chambers may be used. Increasing the number of chambers increases the number of seals necessary to create the chambers.

Figure 10:
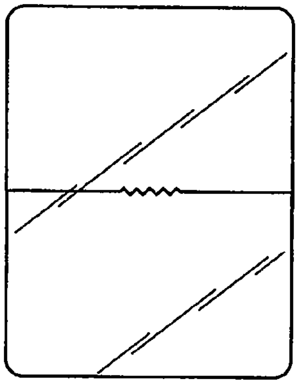
FIG. 10 is a schematic plan view of a peelable seal in accord with an embodiment of the present invention.
Figure 11:
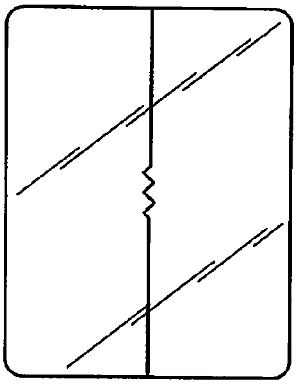
FIG. 11 is a schematic plan view of a peelable seal in accord with an embodiment of the present invention.
Figure 12:
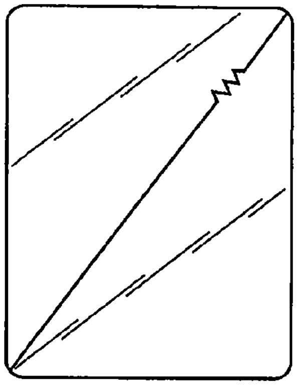
FIG. 12 is a schematic plan view of a peelable seal in accord with an embodiment of the present invention.
Figure 13:
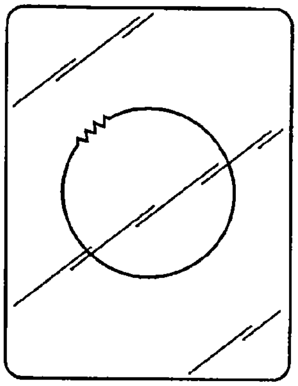
FIG. 13 is a schematic plan view of a peelable seal in accord with an embodiment of the present invention.
Figure 14:
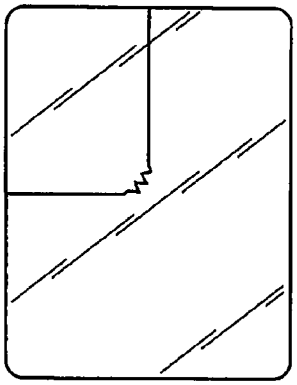
FIG. 14 is a schematic plan view of a peelable seal in accord with an embodiment of the present invention.

The peelable seal 26 connects the first sidewall 12 to the second sidewall 13 of the container 10, and preferably extends between opposing sides of the container periphery or peripheral seal 14. The peelable seal 26 has edges 27 and 29. The peelable seal 26 is shown in FIGS. 1 and 11 as extending along the length dimension of the container, but could also extend between lateral edges as shown in FIG. 10. Alternatively, the peelable seal 26 may be contained completely within the first sidewall 12 and second sidewall 13, and not intersect any part of the peripheral seal 14 (FIG. 13). It is further contemplated that the peelable seal 26 can extend from a corner, a lateral edge, or a longitudinal edge, and terminate elsewhere in the container 10 (FIGS. 12 and 14). The peelable seal 26 may be located anywhere between the first sidewall 12 and second sidewall 13 depending on the relative sizes of the chambers 22 and 24 desired. The chambers 22 and 24 may be filled with medical or other components for forming therapeutic solutions, including intravenous solutions, nutritional solutions, drug solutions, enteral solutions, parenteral solutions, dialysis solutions, pharmacological agents include gene therapy and chemotherapy agents, and many other fluids that may be administered to a patient. The components may be liquid, powder, lyophilized tablet, or other suitable form. The components are introduced to the container 10 and chambers 22 and 24 using any conventional means, such as delivering through a dedicated access port for each chamber 22 and 24. The edges 27 and 29 of the peelable seal 26 abut the fluid in chambers 22 and 24.

The container 10 is preferably made of a flexible polymeric material. Numerous polymeric films have been developed for use in containers. Container films may be a monolayer structure or a multiple layer structure of polymeric materials formed as a pouch or bag. The monolayer structure can be made from a single polymer, or from a polymer blend. Multiple layer structures can be formed by co-extrusion, extrusion lamination, lamination, or any suitable means. The multiple layer structures can include layers such as a solution contact layer, a scratch resistant layer, a barrier layer for preventing permeation of oxygen or water vapor, tie layers, or other layers. Selection of the appropriate film depends on the solution to be contained within the container. Appropriate polymeric materials generally include homopolymers and copolymers of polyolefins, polyamides, polyesters, polybutadiene, styrene and hydrocarbon copolymers.

The seal layer can be a homophase polymer, or a matrix-phase polymer system. Suitable homophase polymers include polyolefins and more preferably polypropylene and most preferably a propylene and ethylene copolymer as described in EP 0875231, which is incorporated herein by reference.

Suitable matrix-phase polymer systems will have at least two components. The two components can be blended together or can be produced in a two-stage reactor process. Typically, the two components will have different melting points. In the case where one of the components is amorphous, its glass transition temperature will be lower than the melting point of the other components. Examples of suitable matrix-phase polymer system includes a component of a homopolymer or copolymer of a polyolefin and a second component of a styrene and hydrocarbon copolymer. Another suitable matrix-phase system includes blends of polyolefins such as polypropylene with polyethylene, or polypropylene with a high isotactic index (crystalline) with polypropylene with a lower isotactic index (amorphous), or a polypropylene homopolymer with a propylene and α-olefin copolymer.

Suitable polyolefins include homopolymers and copolymers obtained by polymerizing alpha-olefins containing from 2 to 20 carbon atoms, and more preferably from 2 to 10 carbons. Therefore, suitable polyolefins include polymers and copolymers of propylene, ethylene, butene-1, pentene-1, 4-methyl-1-pentene, hexene-1, heptene-1, octene-1, nonene-1 and decene-1. Most preferably the polyolefin is a homopolymer or copolymer of propylene or a homopolymer or copolymer of polyethylene.

Suitable homopolymers of polypropylene can have a stereochemistry of amorphous, isotactic, syndiotactic, atactic, hemiisotactic or stereoblock. In a more preferred form of the invention the polypropylene will have a low heat of fusion from about 20 joules/gram to about 220 joules/gram, more preferably from about 60 joules/gram to about 160 joules/gram and most preferably from about 80 joules/gram to about 130 joules/gram. It is also desirable, in a preferred form of the invention, for the polypropylene homopolymer to have a melting point temperature of less than about 165° C. and more preferably from about 130° C. to about 160° C., most preferably from about 140° C. to about 150° C. In one preferred form of the invention the homopolymer of polypropylene is obtained using a single site catalyst.

Suitable copolymers of propylene are obtained by polymerizing a propylene monomer with an α-olefin having from 2 to 20 carbons. In a more preferred form of the invention the propylene is copolymerized with ethylene in an amount by weight from about 1% to about 20%, more preferably from about 1% to about 10% and most preferably from 2% to about 5% by weight of the copolymer. The propylene and ethylene copolymers may be random or block copolymers.

It is also possible to use a blend of polypropylene and α-olefin copolymers wherein the propylene copolymers can vary by the number of carbons in the α-olefin. For example, the present invention contemplates blends of propylene and α-olefin copolymers wherein one copolymer has a 2 carbon α-olefin and another copolymer has a 4 carbon α-olefin. It is also possible to use any combination of α-olefins from 2 to 20 carbons and more preferably from 2 to 8 carbons. Accordingly, the present invention contemplates blends of propylene and α-olefin copolymers wherein a first and second α-olefins have the following combination of carbon numbers: 2 and 6, 2 and 8, 4 and 6, 4 and 8. It is also contemplated using more than 2 polypropylene and α-olefin copolymers in the blend. Suitable polymers can be obtained using a catalloy procedure.

Suitable homopolymers of ethylene include those having a density of greater than 0.915 g/cc and includes low density polyethylene (LDPE), medium density polyethylene (MDPE) and high density polyethylene (HDPE).

Suitable copolymers of ethylene are obtained by polymerizing ethylene monomers with an α-olefin having from 3 to 20 carbons, more preferably 3-10 carbons and most preferably from 4 to 8 carbons. It is also desirable for the copolymers of ethylene to have a density as measured by ASTM D-792 of less than about 0.915 g/cc and more preferably less than about 0.910 g/cc and even more preferably less than about 0.900 g/cc. Such polymers are oftentimes referred to as VLDPE (very low density polyethylene) or ULDPE (ultra low density polyethylene). Preferably the ethylene α-olefin copolymers are produced using a single site catalyst and even more preferably a metallocene catalyst systems. Single site catalysts are believed to have a single, sterically and electronically equivalent catalyst position as opposed to the Ziegler-Natta type catalysts which are known to have a mixture of catalysts sites. Such single-site catalyzed ethylene α-olefins are sold by Dow under the trade name AFFINITY, DuPont Dow under the trademark ENGAGE® and by Exxon under the trade name EXACT. These copolymers shall sometimes be referred to herein as m-ULDPE.

Suitable copolymers of ethylene also include ethylene and lower alkyl acrylate copolymers, ethylene and lower alkyl substituted alkyl acrylate copolymers and ethylene vinyl acetate copolymers having a vinyl acetate content of from about 8% to about 40% by weight of the copolymer. The term "lower alkyl acrylates" refers to comonomers having the formula set forth in Diagram 1:

Diagram 1

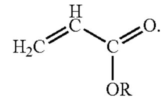

The R group refers to alkyls having from 1 to 17 carbons. Thus, the term "lower alkyl acrylates" includes but is not limited to methyl acrylate, ethyl acrylate, butyl acrylate and the like.

The term "alkyl substituted alkyl acrylates" refers to comonomers having the formula set forth in Diagram 2:

Diagram 2

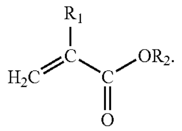

$R_1$ and $R_2$ are alkyls having 1-17 carbons and can have the same number of carbons or have a different number of carbons. Thus, the term "alkyl substituted alkyl acrylates" includes but is not limited to methyl methacrylate, ethyl methacrylate, methyl ethacrylate, ethyl ethacrylate, butyl methacrylate, butyl ethacrylate and the like.

Suitable polybutadienes include the 1,2- and 1,4-addition products of 1,3-butadiene (these shall collectively be referred to as polybutadienes). In a more preferred form of the invention the polymer is a 1,2-addition product of 1,3 butadiene (these shall be referred to as 1,2 polybutadienes). In an even more preferred form of the invention the polymer of interest is a syndiotactic 1,2-polybutadiene and even more preferably a low crystallinity, syndiotactic 1,2 polybutadiene. In a preferred form of the invention the low crystallinity, syndiotactic 1,2 polybutadiene will have a crystallinity less than 50%, more preferably less than about 45%, even more preferably less than about 40%, even more preferably the crystallinity will be from about 13% to about 40%, and most preferably from about 15% to about 30%. In a preferred form of the invention the low crystallinity, syndiotactic 1,2 polybutadiene will have a melting point temperature measured in accordance with ASTM D 3418 from about 70° C. to about 120° C. Suitable resins include those sold by JSR (Japan Synthetic Rubber) under the grade designations: JSR RB 810, JSR RB 820, and JSR RB 830.

Suitable polyesters include polycondensation products of di- or polycarboxylic acids and di or poly hydroxy alcohols or alkylene oxides. In a preferred form of the invention the polyester is a polyester ether. Suitable polyester ethers are obtained from reacting 1,4 cyclohexane dimethanol, 1,4 cyclohexane dicarboxylic acid and polytetramethylene glycol ether and shall be referred to generally as PCCE. Suitable PCCE's are sold by Eastman under the trade name ECDEL.

Suitable polyesters farther include polyester elastomers which are block copolymers of a hard crystalline segment of polybutylene terephthalate and a second segment of a soft (amorphous) polyether glycols. Such polyester elastomers are sold by Du Pont Chemical Company under the trade name HYTREL®.

Suitable polyamides include those that result from a ring-opening reaction of lactams having from 4-12 carbons. This group of polyamides therefore includes nylon 6, nylon 10 and nylon 12. Acceptable polyamides also include aliphatic polyamides resulting from the condensation reaction of di-amines having a carbon number within a range of 2-13, aliphatic polyamides resulting from a condensation reaction of di-acids having a carbon number within a range of 2-13, polyamides resulting from the condensation reaction of dimer fatty acids, and amide containing copolymers. Thus, suitable aliphatic polyamides include, for example, nylon 66, nylon 6,10 and dimer fatty acid polyamides.

Suitable styrene and hydrocarbon copolymers include styrene and the various substituted styrenes including alkyl substituted styrene and halogen substituted styrene. The alkyl group can contain from 1 to about 6 carbon atoms. Specific examples of substituted styrenes include alpha-methylstyrene, beta-methylstyrene, vinyltoluene, 3-methylstyrene, 4-methylstyrene, 4-isopropylstyrene, 2,4-dimethylstyrene, o-chlorostyrene, p-chlorostyrene, o-bromostyrene, 2-chloro-4-methylstyrene, etc. Styrene is the most preferred.

The hydrocarbon portion of the styrene and hydrocarbon copolymer includes conjugated dienes. Conjugated dienes which may be utilized are those containing from 4 to about 10 carbon atoms and more generally, from 4 to 6 carbon atoms. Examples include 1,3-butadiene, 2-methyl-1,3-butadiene (isoprene), 2,3-dimethyl-1,3-butadiene, chloroprene, 1,3-pentadiene, 1,3-hexadiene, etc. Mixtures of these conjugated dienes also may be used such as mixtures of butadiene and isoprene. The preferred conjugated dienes are isoprene and 1,3-butadiene.

The styrene and hydrocarbon copolymers can be block copolymers including di-block, tri-block, multi-block, and star block. Specific examples of diblock copolymers include styrene-butadiene, styrene-isoprene, and the hydrogenated derivatives thereof. Examples of triblock polymers include styrene-butadiene-styrene, styrene-isoprene-styrene, alpha-methylstyrene-butadiene-alpha-methylstyrene, and alpha-methylstyrene-isoprene-alpha-methylstyrene and hydrogenated derivatives thereof.

The selective hydrogenation of the above block copolymers may be carried out by a variety of well known processes including hydrogenation in the presence of such catalysts as Raney nickel, noble metals such as platinum, palladium, etc., and soluble transition metal catalysts. Suitable hydrogenation processes which can be used are those wherein the diene-containing polymer or copolymer is dissolved in an inert hydrocarbon diluent such as cyclohexane and hydrogenated by reaction with hydrogen in the presence of a soluble hydrogenation catalyst. Such procedures are described in U.S. Pat. Nos. 3,113,986 and 4,226,952, the disclosures of which are incorporated herein by reference and made a part hereof.

Particularly useful hydrogenated block copolymers are the hydrogenated block copolymers of styrene-isoprene-styrene, such as a styrene-(ethylene/propylene)-styrene block polymer. When a polystyrene-polybutadiene-polystyrene block copolymer is hydrogenated, the resulting product resembles a regular copolymer block of ethylene and 1-butene (EB). As noted above, when the conjugated diene employed is isoprene, the resulting hydrogenated product resembles a regular copolymer block of ethylene and propylene (EP). One example of a commercially available selectively hydrogenated copolymer is KRATON G-1652 which is a hydrogenated SBS triblock comprising 30% styrene end blocks and a midblock equivalent is a copolymer of ethylene and 1-butene (EB). This hydrogenated block copolymer is often referred to as SEBS. Other suitable SEBS or SIS copolymers are sold by Kurrarry under the tradename SEPTON® and HYBRAR®. It may also be desirable to use graft modified styrene and hydrocarbon block copolymers by grafting an alpha, beta-unsaturated monocarboxylic or dicarboxylic acid reagent onto the selectively hydrogenated block copolymers described above.

The block copolymers of the conjugated diene and the vinyl aromatic compound are grafted with an alpha, beta-unsaturated monocarboxylic or dicarboxylic acid reagent. The carboxylic acid reagents include carboxylic acids per se and their functional derivatives such as anhydrides, imides, metal salts, esters, etc., which are capable of being grafted onto the selectively hydrogenated block copolymer. The grafted polymer will usually contain from about 0.1 to about 20%, and preferably from about 0.1 to about 10% by weight based on the total weight of the block copolymer and the carboxylic acid reagent of the grafted carboxylic acid. Specific examples of useful monobasic carboxylic acids include acrylic acid, methacrylic acid, cinnamic acid, crotonic acid, acrylic anhydride, sodium acrylate, calcium acrylate and magnesium acrylate, etc. Examples of dicarboxylic acids and useful derivatives thereof include maleic acid, maleic anhydride, fumaric acid, mesaconic acid, itaconic acid, citraconic acid, itaconic anhydride, citraconic anhydride, monomethyl maleate, monosodium maleate, etc. The styrene and hydrocarbon block copolymer can be modified with an oil such as the oil modified SEBS sold by the Shell Chemical Company under the product designation KRATON G2705.

The container 10 is typically formed by placing one or more polymeric film sheets forming the first sidewall 12 and second sidewall 13 in registration by their peripheral portions and sealing their periphery 14 to form a fluid tight pouch. The sheets are typically sealed by heat sealing, radio frequency sealing, thermal transfer welding, adhesive sealing, solvent bonding, and ultrasonic or laser welding. Blown extrusion is another method that may be used to make the pouch. Blown extrusion is a process that provides a moving tube of extrudate exiting an extrusion die. Air under pressure inflates the tube. Longitudinal ends of the tube are sealed to form the pouch. Blown extrusion only requires seals along two peripheral surfaces, where the single or multiple sheet registration method requires seals along one, three, or four peripheral surfaces to form the pouch.

The peelable seal 26 is preferably created by heat sealing, but may be made by any of the above-mentioned sealing or welding methods, or any other suitable method. The peelable seal 26 is peelable such that it may be peeled by hand pressure to separate the first sidewall 12 and second sidewall 13 to allow fluid communication between the first chamber 22 and second chamber 24, thereby mixing the components contained in them. The peelable seal 26 is peeled, for example, by gripping the first sidewall 12 and second sidewall 13 of the container 10, and pulling them apart, or by squeezing or pressing the first sidewall 12 and second sidewall 13 to force the fluid in chambers 22 and 24 against the peelable seal 26 with sufficient force to separate peelable seal 26. The peelable seal 26 is strong enough to withstand external stresses without peeling resulting from ordinary squeezing during handling, shipment, or from accidental dropping.

Containers are often filled at pressures of up to 60 pounds per square inch (psi). After being filled with solution, the container 10 is typically sterilized using steam. The sterilization typically occurs at a temperature of 121° C.

Figure 2:
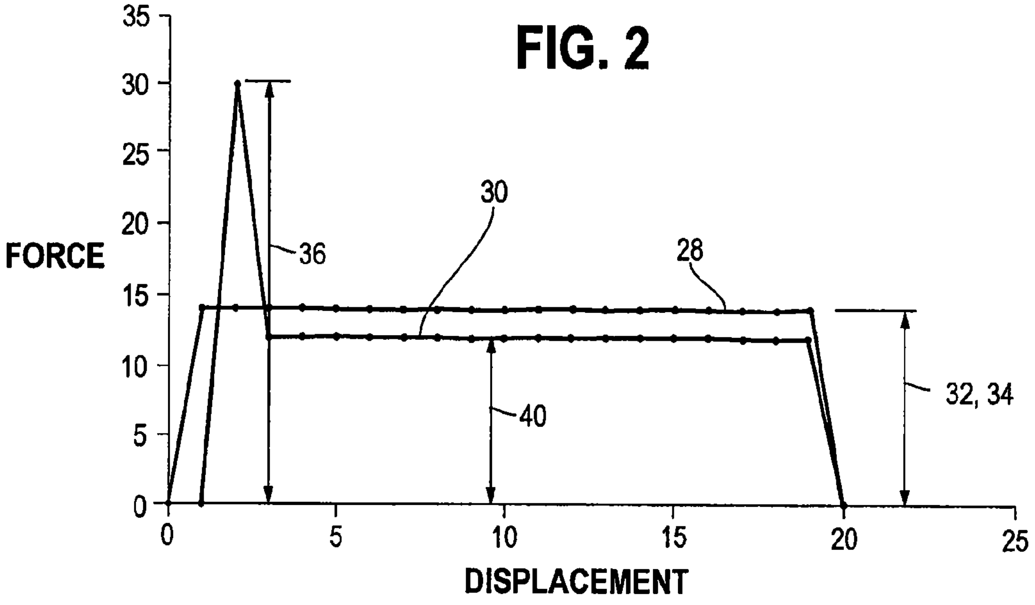
FIG. 2 is a graph showing typical force vs. displacement curves for a peelable seal before and after sterilization.

FIG. 2 shows typical force vs. displacement graph for a peelable seal 26 having straight edges 27 and 29. The x axis of FIG. 2 shows displacement along the length of the peelable seal 26. The y axis shows force necessary to peel the peelable seal 26 at specific points along its length. Curve 28 is the force vs. displacement curve before steam sterilization. Curve 30 is the force vs. displacement curve after steam sterilization. As can be seen from curve 28 of FIG. 2, a force 32 is necessary to initiate peeling the peelable seal 26 prior to steam sterilization. This force 32 is the same as a plateau force 34, which is necessary to propagate peeling after initiation.

As curve 30 shows, after steam sterilization, a peak peel force 36 is required to initiate peeling the peelable seal 26. The peak peel force 36 is significantly greater than a plateau force 40 necessary to propagate peeling. The peak peel force 36 occurs due to sterilization. Sterilization can cause boiling of the solution in the chambers 22 and 24 of the container 10. Boiling can cause expansion of the fluids in the chambers 22 and 24, and thereby further stresses the first sidewall and second sidewall 12 and 13 by forcing them apart. When stress is applied to the peelable seal 26 at a temperature above the softening point of the container material, deformation at the seal edges 27 and 29 occurs. Deformation can also occur because of water expansion and/or shrinkage of the container material due to crystallization, or in the case of stretched container films, stress relaxation. This deformation reduces stress concentration at the seal edges 27 and 29, thereby increasing the force necessary to break the peelable seal 26 to initiate the peeling process. This peak peel force 36 is detrimental to ease of use. Moreover, because of the variable nature of the causes, the peak peel force 36 is variable and hard to control. Some seals 26 may be too easy to activate, peeling during shipping, ordinary handling, or by dropping. Other seals 26 may become almost impossible to initiate peeling by hand.

The present invention overcomes these problems by reducing the peak peel 36 force necessary to initiate peeling at the seal edges 27 and 29. It has been found that changing the shape of the seal edges 27 or 29 from a straight edge on at least the portion of the peelable seal 26 where peeling is to be initiated accomplishes this. This reduces the length of the peelable seal 26 that is subject to stress during exposure to high temperatures during steam sterilization. Thus, the peak peel force 36 occurs only on limited portions of the peelable seal 26.

Figure 3:
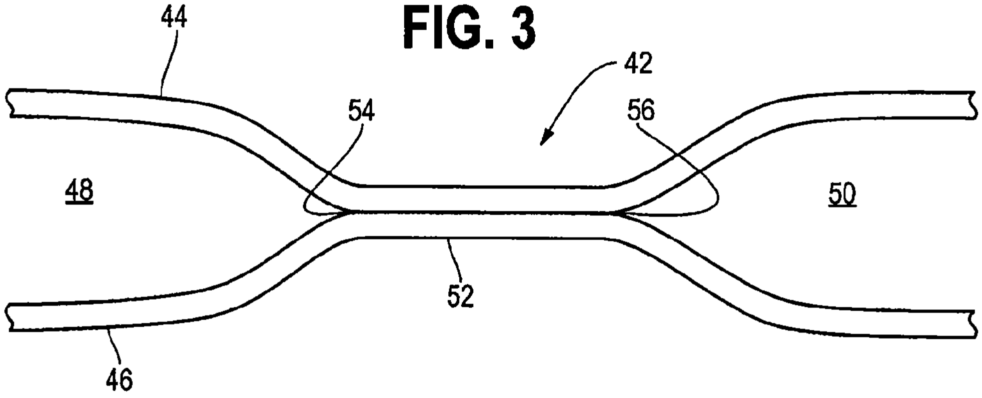
FIG. 3 is a cross-sectional view of a peelable seal having a serrated edge in accord with an embodiment of the present invention.

FIG. 3 shows a cross-sectional view of a peelable seal 42 in accord with an embodiment of the present invention prior to steam sterilization. First sidewall 44 and second sidewall 46 of a container are sealed at the seal 42. The seal 42 defines chambers 48 and 50 in the container.

Figure 4:
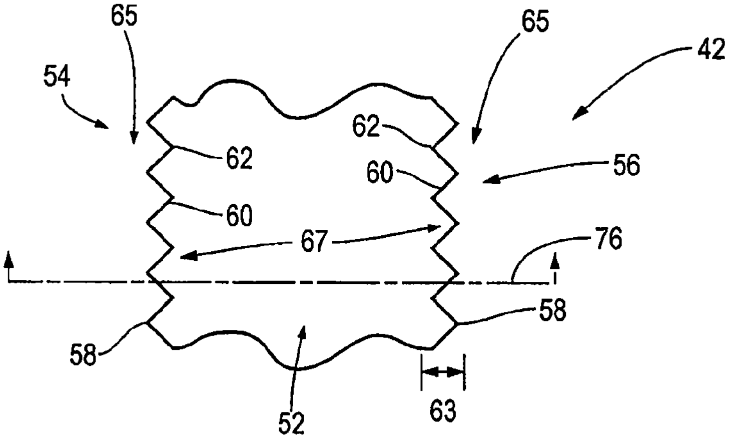
FIG. 4 is an enlarged top view of a peelable seal in accord with an embodiment of the present invention.
Figure 15:
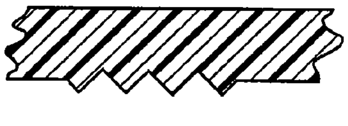
FIG. 15 is a schematic top view of a peelable seal in accord with an embodiment of the present invention.

FIG. 4 is an enlarged top view of the seal 42 of FIG. 3 before steam sterilization. The seal 42 has a sealed area 52, a first seal edge 54, and a second seal edge 56. The first seal edge 54 and second seal edge 56 are serrated, having outer points 58 and angular legs 60 extending at angles from and between the outer points 58. The legs 60 intersect at inner points 62 thereby connecting with outer points 58. Between the inner points 62 and outer points 58 is a depth 63. Though FIG. 4 shows both first seal edge 54 and second seal edge 56 serrated, it is contemplated that only one or the other of the first seal edge 54 or second seal edge 56 may be serrated in accord with the present invention (FIG. 15). It also is contemplated that the serrations can occur over the entire length of the seal 42 or only on selected sections. It is preferred that the serrations be spaced from the peripheral seal 14 of the container 10 to permit peeling.

Figure 5:
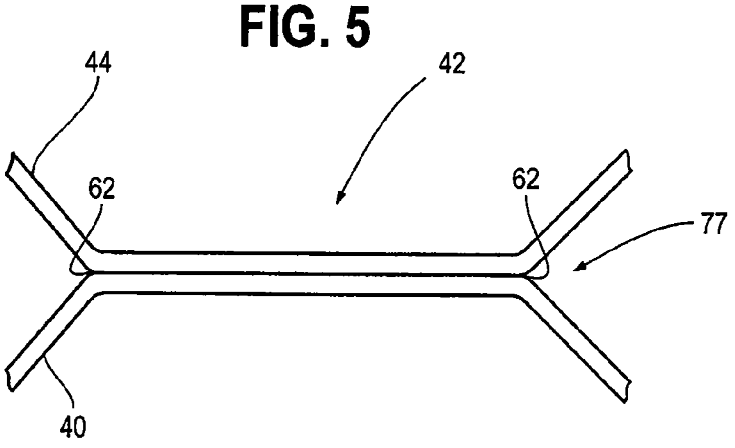
FIG. 5 is a cross-sectional view of a peelable seal in accord with an embodiment of the present invention after streriliza-tion.

FIG. 5 shows a cross-sectional view of the seal 42 after steam sterilization taken along line 76 of FIG. 4 intersecting inner points 62. As shown in FIG. 5, an angular joint 77 between the first sidewall 44 and second sidewall 46 occurs at the inner points 62, and is maintained after steam sterilization.

Figure 6:
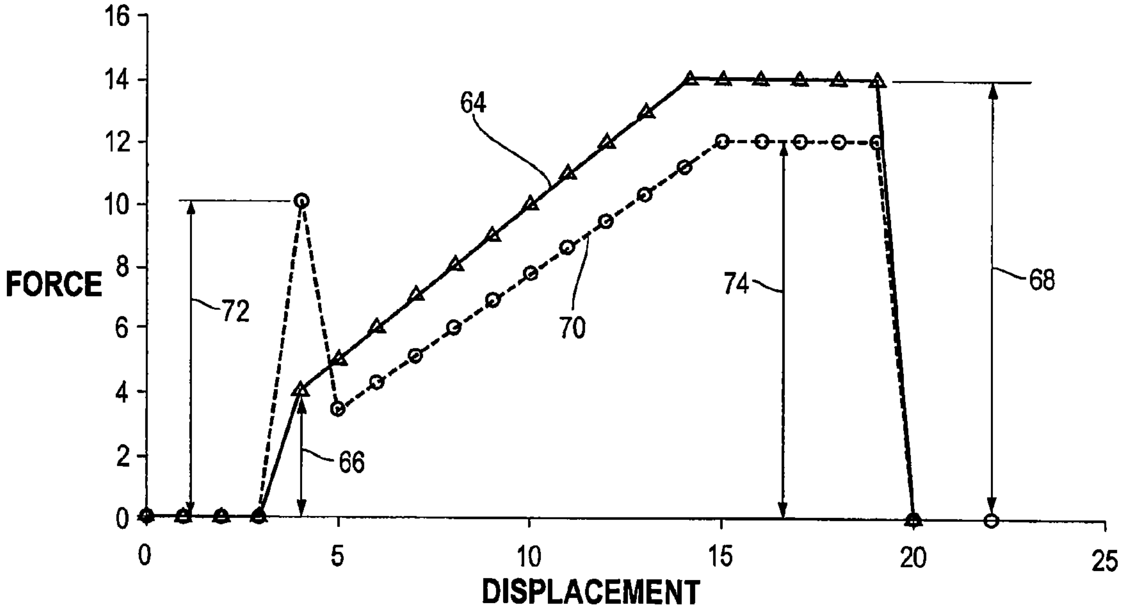
FIG. 6 is a force vs. displacement graph for a peelable seal in accord with an embodiment of the present invention.

FIG. 6 is a force vs. displacement graph for the serrated peel seal 42 of an embodiment of the present invention. The x axis shows displacement along the length of the seal 42. The y axis shows the force required to peel the seal 42 at points along the length of the seal 42. Curve 64 is the force vs. displacement curve before steam sterilization. An initiation force 66 is necessary to initiate propagation. This force increases essentially linearly to a maximum plateau force 68 to propagate the peeling.

FIG. 6 also shows a curve 70 showing force vs. displacement for the serrated peel seal 42 after steam sterilization. Curve 70 demonstrates the peak peel force 72. The peak peel force 72 is greater than the initiation force 66 before sterilization, however, it is less than a maximum propagation force 74 necessary to continue the peeling process. This results in a greater ease of use of the container because less force is required initiate the peeling process than with a seal with straight seal edges.

During sterilization, only the outer points 58 are subject to stress and deformation, and not the inner points 62 or angular legs 60. The outer points 58 are subject to stress because the film tension is at a maximum at the outer points 58. Thus, the stress concentrations present when the seal 42 is made is reduced only at the outer points 58, and not at the angular legs 60 or the inner points 62. Stress concentration is, therefore, retained at inner points 62.

The outer points 58 define an outer stress bearing zone 65 of the peelable seal 42. The outer points 58 bear the stress caused by steam sterilization. The inner points 62 and angular legs 60 define an inner non-stress bearing zone 67 of the seal 42. Creation of a stress-bearing zone may also be accomplished using other shaped seal edges, such as a scalloped seal edge (FIGS. 16 and 18) or a trapezoidal seal edge (FIG. 17), other polygonal or geometric shape.

Figure 16:
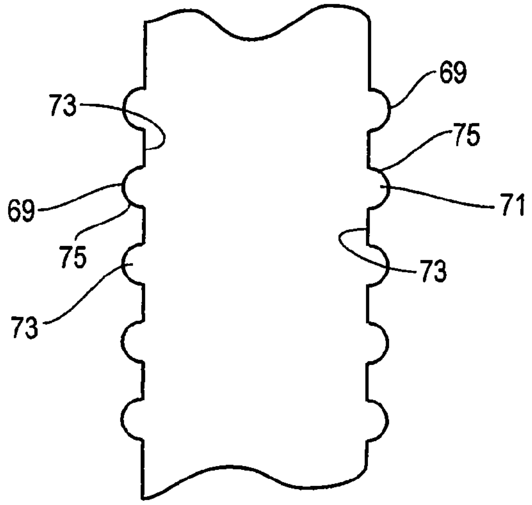
FIG. 16 is a schematic view of a peelable seal in accord with an embodiment of the present invention.
Figure 17:
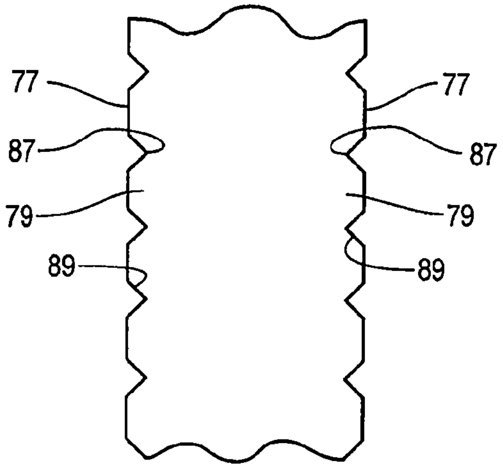
FIG. 17 is a schematic view of a peelable seal in accord with an embodiment of the present invention.
Figure 18:
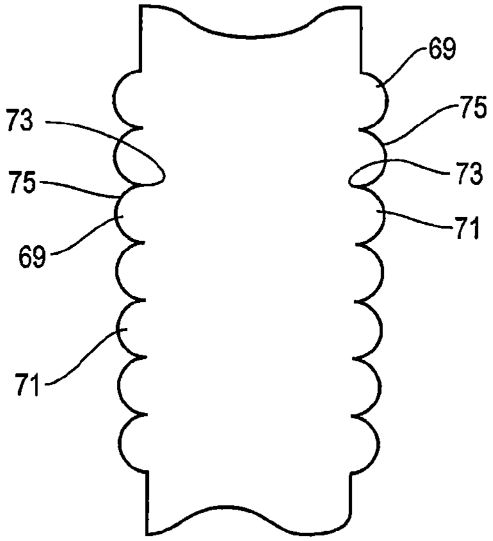
FIG. 18 is a schematic view of a peelable seal in accord with an embodiment of the present invention.

The stress bearing zone in FIGS. 16 and 18 are the crests 69 of the scallops 71. The non-stress bearing zone includes the troughs 73 and sloping sides 75 of the scallops 71. The stress-bearing zone in FIG. 17 is created by the flat portions 77 of the trapezoids 79. The non-stress bearing zone includes the inner points 87 and sides 89 of the trapezoids 79. The present invention also contemplates other seal edge shapes that create an stress bearing zone and a non-stress bearing zone.

In the serrated seal embodiment of FIG. 4, the first sidewall 44 and second sidewall 46 of the container are separated first at the inner points 62. The angular joint 77 at inner points 62 further facilitate separation of the first sidewall 44 and second sidewall 46. As a result, the peak peel force 72 is lower than plateau force 74 for propagating the seal 42, which is the sum of the individual forces required to break the seal 42 at inner points 62, legs 60 and outer points 58. Because the outer points 58 are a small length compared to the overall length of the seal 42, the contribution of the points 58 is small when compared to that contributed by the inner points 62 and legs 60. Hence, the plateau force 74 is reduced compared to a peelable seal 26 having straight edges 27 and 29. This improves the use of the container 10 by permitting the user to easily initiate the peeling process. It also improves the reproducibility of the peak peel force 72. Yet the seal 42 is strong enough to protect the seal 42 against peeling during normal handling. Likewise for scalloped (FIGS. 16 and 18) and trapezoidal (FIG. 17) seal edges, the sidewalls of the container are initially separated at the non-stress bearing zone such that the peak peel force is lower than the plateau force.

For the serrated seal edge embodiment of FIG. 4, an important factor in reducing the peak peel force 72 is the depth 63 of the serrations. The depth 63 controls the slope of the peel force curve 70 before reaching the plateau value 74. The depth 63 must be sufficiently great to permit separation between the peak peel force 72 and the plateau force 74. The minimum depth for reducing the peak peel force 72 is highly dependent on plateau seal force 74 values, i.e., for lower peak peel forces, a greater depth 63 is necessary. Other factors include, mechanical properties of the materials making the container 10, filling volume, filling pressure, and stress occurring during the sterilization process. The greater the volume, the higher the initiation force, and the higher the filling pressure, the higher the initiation force. The number of serrations per unit length is a factor in determining the reduction of the peak peel force 72. The greater the number of serrations, the greater the peak peal force 72. A balance must be struck between peeling force and ability of the seal to withstand normal handling. Experiments have indicated that symmetrical serrations angled at 90 degrees, outer points 58 spaced 8 mm apart, and a depth 63 of 4 mm achieve an acceptable peak peel force 72. Similarly, for embodiments such as the scalloped (FIGS. 16 and 18) or trapezoidal shaped (FIG. 17) seal edges, the depth between the stress-bearing zone and the non-stress-bearing zone must be controlled to balance peeling force and normal handling.

Figure 7:
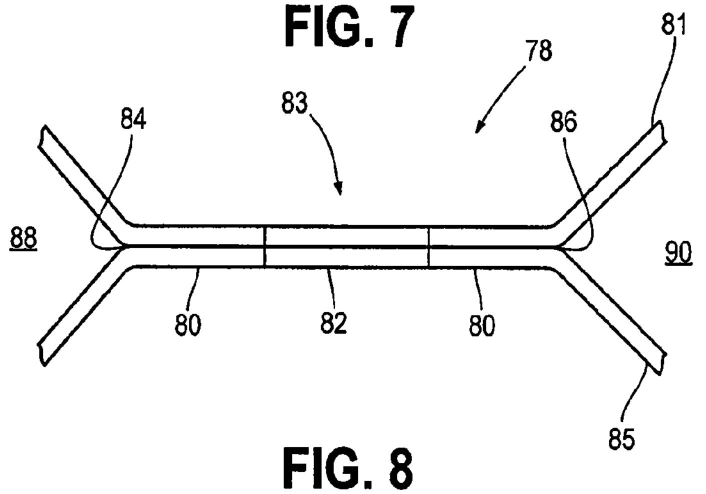
FIG. 7 is a cross-sectional view of a peelable seal in accord with an embodiment of the present invention.

In another embodiment, the present invention includes a seal 78. FIG. 7 shows a cross-sectional view of the seal 78 before steam sterilization. The seal 78 includes a first seal 80 and a second seal 82. The second seal 82 is preferably located at the central portion 83 of the first seal 80. The container 10 has a first sidewall 81 and a second sidewall 85. The seal 78 separates chambers 88 and 90 of the container 10. The first seal 80 also has a lower peel force than the second seal 82. Preferably, the first seal separation force is on the order of 5 N/15 mm, while the second seal separation force is on the order of 15 N/15 mm. The seal 78 is created preferably by heat sealing the first sidewall and second sidewall 81 and 85, and by varying the temperature along the seal 78, such that the temperature to create seal 82 is greater than that for the first seal 80. This causes the first sidewall and second sidewall 81 and 85 at the second seal 82 to adhere together more at the second seal 82 than the first seal 80. In turn, this requires a greater force to separate the first sidewall and second sidewall 81 and 85 at the second seal 82 than the first seal 80. The first seal 80 has a first edge 84 and a second edge 86 that are each in contact with fluid in chambers 88 and 90.

Figure 8:
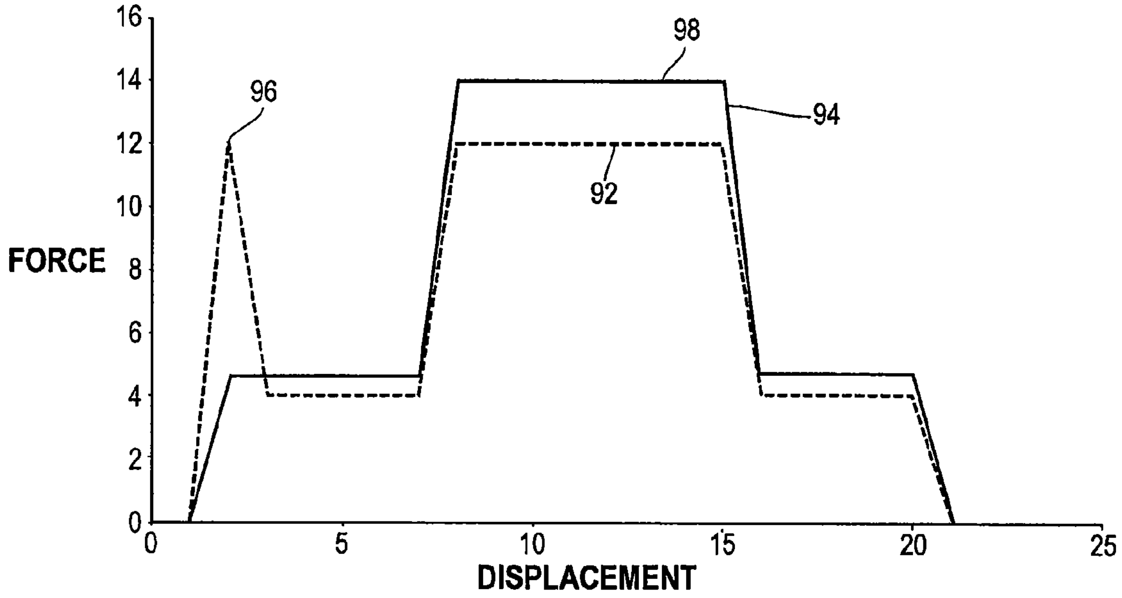
FIG. 8 is force vs. displacement graph for the seal of FIG. 7.

FIG. 8 shows a force vs. displacement graph for the seal 78. Curve 92 shows force vs. displacement before steam sterilization. Curve 94 shows force vs. displacement after steam sterilization. As FIG. 8 demonstrates, the initial peak force 96 after steam sterilization remains lower than maximum plateau force 98 of the second seal 82.

When sterilized, deformation will occur at the first and second edges 84 and 86. This will increase the peel force at first and second edges 84 and 86 of the first seal 80. Thus, even if a peak peel force at first and second edges 84 and 86 appears as high as three times the plateau value of the first seal 80, it will remain below the peel seal force required to separate the second seal 82 in the central portion. Thus, no peek peel force will occur in the second seal 82. The seal 78 is created by heat sealing the second seal 82 at a higher temperature than the first seal 80.

Figure 9:
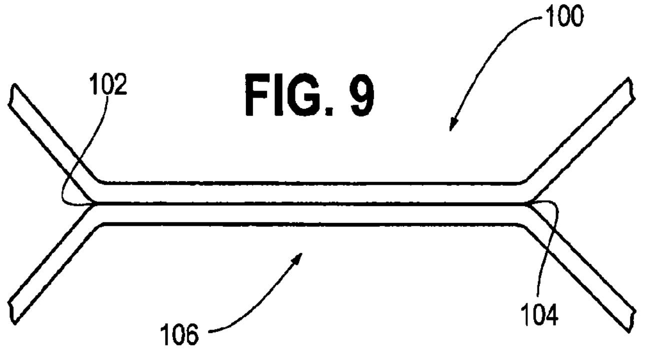
FIG. 9 is a cross-sectional view of a peelable seal in accord with an embodiment of the present invention.

On a similar principle, an another embodiment shown in FIG. 9, a seal 100 has a peeling force gradient along the width of the seal 100. The seal 100 has first and second edges 102 and 104, and a central portion 106 between the first and second edges 102 and 104. The peel force at the first and second edges 102 and 104 is less, preferably approximately three times less, than the peel force at the central portion 106. As for seal 78 described above, the seal 100 is created by a heat seal having a temperature gradient across its width, greater in the middle and less at the edges. A gradient can be obtained, for instance, by a die having heating elements separated by an insulating material layer, and where the temperature of the central heating element is greater than at the edges. Thus, when a peak peal force occurs at the edges 102 and 104, it remains below the peel force at the central portion 106. The peel force at the edges 102 and 104 preferably being approximately 5 N/15 mm and at the central portion 106 being approximately 15 N/15 mm. In this manner, even if the edges 102 and 104 of the seal 100 experience a peel force increase of three times, it is still the same or less than that in the central portion 106. Thus, no peak peal force occurs.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A multichambered container comprising:

a first sidewall and an opposing second sidewall, the sidewalls permanently sealed along a common peripheral edge;

a peelable seal connecting the first sidewall and the second sidewall to form chambers in the container; and the peelable seal having a length, the peelable seal having a serrated portion and a non-serrated portion along at least a portion of the length of the peelable seal, the serrated portion having a shorter length than the non-serrated portion.

2. The container of claim 1 wherein the peelable seal has a first edge, the serrated portion located on the first edge.

3. The container of claim 1 wherein the peelable seal has a first edge and a second edge, the serrated portion located on the first edge and the second edge.

4. The container of claim 1 wherein the serrated portion does not contact the peripheral edge.

5. The container of claim 1 further comprising a medical solution in the container.

6. The container of claim 1 wherein the container is a steam sterilizable container.

7. The container of claim 1 wherein each sidewall has a structure selected from the group consisting of a monolayer structure and a multiple layer structure.

8. The container of claim 1 wherein each sidewall further comprises a seal layer including a material selected from the group consisting of a homophase polymer and a matrix-phase polymer.

9. The container of claim 1 wherein the peel seal forms a chamber having a point, the serrated portion located at the point.

10. A multichambered container comprising:

a first sidewall and an opposing second sidewall;

a peripheral seal sealing the sidewalls along a common peripheral edge;

a peelable seal connecting the first sidewall and the second sidewall to form chambers in the container; and the peelable seal having a length, the peelable seal having a serrated portion and a non-serrated portion along at least a portion of the length of the peelable seal, the serrated portion having a shorter length than the non-serrated portion, the serrated portion not in contact with the peripheral seal.

11. The container of claim 10 wherein the container is enclosed when the peel seal is separated.

12. The container of claim 10 wherein the peelable seal forms a chamber having a point, the serrated portion located at the point.

13. The container of claim 10 wherein the peelable seal extends from a corner of the container.

14. A multichambered container comprising:

a first sidewall and an opposing second sidewall;

a peripheral seal sealing the sidewalls along a common peripheral edge;

a peelable seal forming chambers in the container, the peelable seal having a length, the peelable seal having a serrated portion and a non-serrated portion along at least a portion of the length of the peelable seal, the serrated portion having a shorter length than the non-serrated portion; and the peelable seal not in contact with the peripheral seal.

* * * * *